United States Patent
Geiselhart et al.

(10) Patent No.: US 9,078,663 B2
(45) Date of Patent: Jul. 14, 2015

(54) ELECTROSURGICAL DEVICE, METHOD FOR GENERATING A PRESCRIBED HEAT DISTRIBUTION OVER A PROBE BODY, METHOD FOR GENERATING A HEAT DISTRIBUTION FIELD

(75) Inventors: Franz Geiselhart, Reutlingen (DE); Matthias Voigtländer, Gomaringen (DE); Horst Kegreiss, Tübingen (DE)

(73) Assignee: ERBE ELEKTROMEDIZIN GMBH, Tucbingen (DE)

( * ) Notice: Subject to any disclaimer, the term of this patent is extended or adjusted under 35 U.S.C. 154(b) by 1103 days.

(21) Appl. No.: 13/003,511

(22) PCT Filed: Jun. 23, 2009

(86) PCT No.: PCT/EP2009/004525
§ 371 (c)(1),
(2), (4) Date: Mar. 15, 2011

(87) PCT Pub. No.: WO2010/003547
PCT Pub. Date: Jan. 14, 2010

(65) Prior Publication Data
US 2011/0160722 A1  Jun. 30, 2011

(30) Foreign Application Priority Data

Jul. 10, 2008 (DE) .......................... 10 2008 032 512
Sep. 1, 2008 (DE) .......................... 10 2008 045 268

(51) Int. Cl.
*A61B 18/18* (2006.01)
*A61B 18/14* (2006.01)
(Continued)

(52) U.S. Cl.
CPC ...... *A61B 18/148* (2013.01); *A61B 2018/00023* (2013.01); *A61B 2018/0268* (2013.01)

(58) Field of Classification Search
CPC ..................... A61B 18/148; A61B 2018/0268; A61B 2018/00023
USPC ......................................... 606/20–26, 38–45
See application file for complete search history.

(56) References Cited

U.S. PATENT DOCUMENTS

| | | | |
|---|---|---|---|
| 4,946,460 | A | 8/1990 | Merry et al. |
| 5,697,927 | A | 12/1997 | Imran et al. |
| 6,471,693 | B1 | 10/2002 | Carroll et al. |

(Continued)

FOREIGN PATENT DOCUMENTS

| | | |
|---|---|---|
| DE | 693 30 821 T2 | 5/2002 |
| JP | H02-299647 | 12/1990 |

(Continued)

*Primary Examiner* — Joseph Stoklosa
*Assistant Examiner* — Amanda Scott
(74) *Attorney, Agent, or Firm* — Dickstein Shapiro LLP

(57) ABSTRACT

An electrosurgical device for devitalizing tissue including a probe body, equipped with at least one electrode, and a cooling device. The probe body is suitable for generating a heat distribution field by means of a high-frequency current for devitalizing the tissue. The cooling device prevents carbonization of the tissue close to the probe body that would normally occur since the maximum current density occurs here. The electrosurgical device is modified such that the heat distribution over the probe body can be adjusted, allowing adjustment or positioning of a maximum cooling zone within the probe body. This regulation may be accomplished by regulating the inlet pressure of the refrigerant supply to the electrosurgical device.

12 Claims, 3 Drawing Sheets

(51) Int. Cl.
*A61B 18/00* (2006.01)
*A61B 18/02* (2006.01)

(56) References Cited

U.S. PATENT DOCUMENTS

2002/0111615 A1  8/2002  Cosman et al.
2005/0010201 A1  1/2005  Abboud et al.
2006/0271034 A1  11/2006  Swanson
2007/0149959 A1  6/2007  DeLonzor et al.
2008/0154258 A1  6/2008  Chang et al.

FOREIGN PATENT DOCUMENTS

| JP | 2001-510702 A | 8/2001 |
| WO | WO 99/04710 A1 | 2/1999 |
| WO | WO 01/41664 A1 | 6/2001 | ures
ELECTROSURGICAL DEVICE, METHOD FOR GENERATING A PRESCRIBED HEAT DISTRIBUTION OVER A PROBE BODY, METHOD FOR GENERATING A HEAT DISTRIBUTION FIELD

FIELD OF THE DISCLOSED EMBODIMENTS

The disclosed embodiments relate to an electrosurgical device for devitalizing tissue, a method for generating a prescribed heat distribution using such an electrosurgical device and a method for generating a heat distribution field using such an electrosurgical device.

BACKGROUND

Electrosurgical devices, and particularly probes for devitalizing tissue (ablation probes), are known which include a probe body with at least one electrode for applying a high-frequency current and a cooling device. The high-frequency current is generated via a high frequency generator.

In high-frequency surgery, an alternating current is passed through the human body at a high frequency in order to selectively damage tissue. One application of high frequency surgery is the devitalizing of tumor tissue. High frequency surgery utilizes the thermal effect of heating by which devitalizing of tissue is achieved.

A distinction is drawn between a bipolar and a monopolar application of the high-frequency current. In a monopolar application, the instrument of the electrosurgical device includes only one electrode, while a second, neutral electrode is placed directly on the patient. The current flows, in an inversely proportional relationship to the resistance in the tissue, from the electrode of the instrument to the neutral electrode. In the immediate vicinity of the electrode of the instrument, the current density is high enough for the described thermal effect to occur. With increasing distance from this electrode, the current density falls off in inverse square relation thereto. The devitalizing effect of the high-frequency current is therefore spatially limited.

With a bipolar application, the instrument includes two electrodes. For example, a probe tip can be configured as a first electrode, while a proximal section of the probe serves as the second electrode. The high-frequency current or high-frequency voltage is applied between the two electrodes, which are insulated from one another. The circuit is completed through the tissue that is situated therebetween. A current distribution field is produced which is concentrated in the immediate vicinity of the probe.

It is self-evident that, regardless of the start of application of the high-frequency current, a high field density forms in the immediate vicinity of the instrument. This high field density can lead to carbonization of the surrounding tissue. This carbonization is undesirable, at least in the devitalizing of tumors, since a layer formed in this way has a strongly insulating effect and hinders the treatment in deeper tissue regions. In addition, the body cannot readily decompose such carbonized tissue.

For this reason, the cooling device is used to cool the immediately adjacent tissue to prevent dehydration and/or carbonization of the adjacent tissue.

When devitalizing tumor tissues with the aid of an ablation probe, it can arise that adjacent structures (e.g. blood vessels, lymph ducts, organs), impair the current distribution, and thus the heat distribution, close to the probe. In the case of monopolar probes, the position of the neutral electrode relative to the probe or the instrument can lead to an unwanted current distribution within the tissue. It is thus desirable, for example, when treating tumors, to provide a heat distribution field that is as even as possible, and is preferably spherical, in order to devitalize the tumor completely.

SUMMARY

Proceeding from this prior art, it is an object of the disclosed embodiments to provide an improved electrosurgical device for devitalizing tissue. In particular, conventional electrosurgical devices are to be improved such that said devices generate a prescribed heat distribution field for devitalizing the tissue. Furthermore, a method for generating a prescribed heat distribution over a probe body and a method for generating a heat distribution field are to be provided.

One disclosed embodiment includes an electrosurgical device and, more particularly a probe for devitalizing tissue, including a probe body; at least one electrode for applying a high-frequency current to the tissue, by means of which, tissue heating or a heat distribution field can be generated for devitalizing the tissue; a cooling device for influencing the heat distribution field, wherein said cooling device has an evaporation region, which is supplied with a fluid via an inlet to cool at least part of the probe body; and an outlet to remove the fluid from the evaporation region, wherein the evaporation region is configured such that the heat distribution over the probe body is adjustable by varying an inlet pressure in the inlet and/or an outlet pressure in the outlet.

In the disclosed embodiments, the heat distribution field generated by means of the high-frequency current is influenced by a prescribed heat distribution over the probe body. The heat distribution field can thus be adjusted to the local conditions. In particular, structures which have a different conductivity from the other tissues and influence the current distribution field are taken into account. In monopolar instruments, it is possible to adjust the heat distribution via the probe body such that varying distances between sections of the electrode on the instrument and the neutral electrode do not, or only slightly, influence the heat distribution field.

According to the disclosed embodiments, the heat distribution over the probe body, or over parts thereof, can be set by varying the inlet pressure and/or the outlet pressure of the cooling fluid.

The electrosurgical device can include an adjusting device for adjusting the inlet pressure and/or the outlet pressure. It is conceivable for the regulation of the pressure conditions or the inlet pressure or the outlet pressure to be carried out in an external device. Alternatively, the electrosurgical device according to the disclosed embodiments includes an adjusting device, for example, a valve, in order to adjust the inlet or outlet pressure.

The evaporation region can include at least one resistance element or swirling element, which divides the evaporation region into at least one distal region and one proximal region and is configured such that the pressure conditions vary, with increasing inlet pressure, between the proximal region and the distal region.

To provide the cooling effect, either a vapor-compression refrigeration unit or the Joule-Thomson effect can be used. With both processes, the cooling power provided depends essentially on the pressure conditions within the evaporation region. The disclosed embodiments provide for at least one swirling element or resistance element arranged within the evaporation region, which divides the evaporation region into at least two pressure regions, specifically the proximal pressure region and the distal pressure region. Depending on the inlet pressure or the outlet pressure, the pressure conditions can differ between the proximal pressure region and the distal pressure region. For example, given a low inlet pressure, wherein only a little fluid is introduced into the evaporation region, the flow resistance of the swirl element can be negligibly low. The pressure in the proximal pressure region therefore differs only slightly from the pressure in the distal pressure region. If the pressure in the inlet is increased, the flow resistance increases depending on the design of the resistance or the swirling element of the flow resistance. Since the inlet opens into the distal pressure region, a significantly higher pressure can exist here than in the proximal pressure region. At a given temperature, for a refrigerant, this can mean that the refrigerant does not evaporate or only partially evaporates in the distal pressure region, whereas in the proximal pressure region, complete evaporation takes place. A corresponding change in the pressure conditions depending on the outlet pressure or a relation between the inlet pressure and the outlet pressure can also be ensured.

The evaporation region can further include a plurality of resistance and/or swirl elements, which are arranged and configured such that at least one main pressure gradient is formed in the evaporation region, depending on the inlet pressure and/or the outlet pressure, particularly along a longitudinal axis of the probe. The evaporation region can therefore be configured so that a defined flow resistance exists along the flow direction of the fluid. For example, a plurality of resistance elements can be arranged therein, which, depending on the inlet pressure and/or the fluid volume introduced, induce a different flow resistance. It is therefore possible to vary the main pressure gradient depending on the inlet pressure and/or the outlet pressure. In each case, the maximum cooling effect will arise wherever the main pressure gradient falls below a boiling pressure or a boiling pressure region. It is therefore possible to appropriately position the maximum cooling effect within the probe body, depending on need.

Where the probe has an elongate form and a longitudinal axis and the evaporation region is configured along said longitudinal axis, depending on the inlet pressure and/or the outlet pressure, the main gradient can be adjusted so that the refrigerant evaporates close to the proximal or distal end of the probe. A continuously regulable position is conceivable.

At least one of the swirling elements can include an expansion element, particularly an expansion nozzle. For example, the fluid can be introduced via this expansion nozzle into the evaporation region. Depending on the setting of the inlet pressure and/or the outlet pressure, a boiling pressure is produced immediately behind the expansion nozzle. By adjusting the inlet pressure and/or the outlet pressure, the boiling pressure can be displaced along the direction of flow. For example, by increasing the inlet pressure, the flow resistance can be increased at the subsequent swirl elements such that the boiling pressure falls off strongly only after these swirl elements, such that evaporation takes place.

The electrosurgical device can include a control device which adjusts the high-frequency current heating the tissue, and which adjusts the inlet pressure and/or the outlet pressure determining the cooling of the probe, such that, on application of the high-frequency current, a prescribed heat distribution field, particularly a spherical heat distribution field, is produced in the tissue. For example, it can be helpful, in the treatment of tumors, if a heat distribution field forms which is symmetrical, particularly spherical. The heat distribution field can be defined such that the region concerned is the three-dimensional region close to the probe body, which is heated by the high-frequency current. In particular, the heat distribution field can be defined such that the tissue within this region is strongly heated so that it undergoes devitalization.

Disclosed embodiments also include a method for generating a prescribed heat distribution over a probe body of an electrosurgical device. The method includes the following steps: feeding in a fluid for cooling the probe body, via an inlet; introducing the fluid into an evaporation region from which heat is extracted by the fluid; removing the fluid via an outlet; and adjusting a main pressure gradient in the evaporation region by varying an inlet pressure in the inlet and/or an outlet pressure in the outlet, in order to generate the prescribed heat distribution.

In the provision of the heat distribution, a central concept of the disclosed embodiments lies in positioning the maximum cooling effect by adjusting the main pressure gradient. Depending on the configuration of the main pressure gradient, the boiling of the refrigerant takes place at a different position in the evaporation region.

Disclosed embodiments also include a method for generating a heat distribution field within a tissue. The method includes the following steps: heating the tissue by the application of a high-frequency current by means of an electrosurgical device; cooling the tissue by means of a probe body of the electrosurgical device, wherein the cooling includes generating a prescribed heat distribution over the probe body, as described previously.

BRIEF DESCRIPTION OF THE DRAWINGS

The disclosed embodiments will be described in greater detail, pointing out further features and advantages, by reference to the example embodiments illustrated in the drawings.

DETAILED DESCRIPTION

In the following description, the same reference numbers are used for the same and similarly acting parts.

Figure 1:
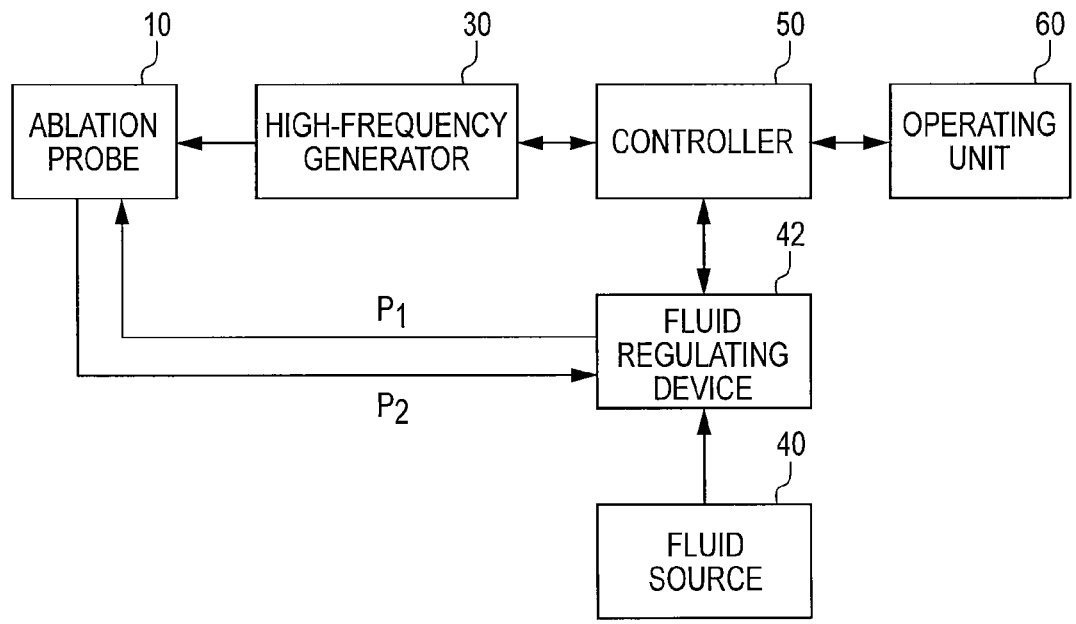
FIG. 1 illustrates essential components of an electrosurgical device in accordance with disclosed embodiments.

FIG. 1 shows the essential components of an electrosurgical device according to the disclosed embodiments. An ablation probe 10 is typically supplied with fluid from a fluid source 40. In order to adjust a prescribed inlet pressure P1 and/or outlet pressure P2, the fluid source 40 is in fluid connection with a fluid regulating device 42, which can include a plurality of valves and measuring sensors.

A high-frequency generator 30 is in electrical connection with the ablation probe 10 and provides a high-frequency current which is applied via appropriate electrodes 16, 16'

(see FIG. 2) or 16" (see FIG. 4) to a tissue 1 to be treated. The electrosurgical device also includes a controller 50 which controls the high-frequency generator 30 and the fluid regulating device 42. The controller 50 receives signals from an operating unit 60, via which the treating physician can make settings on the electrosurgical device. For example, the coagulation process can be started via the operating unit 60.

Figure 2:
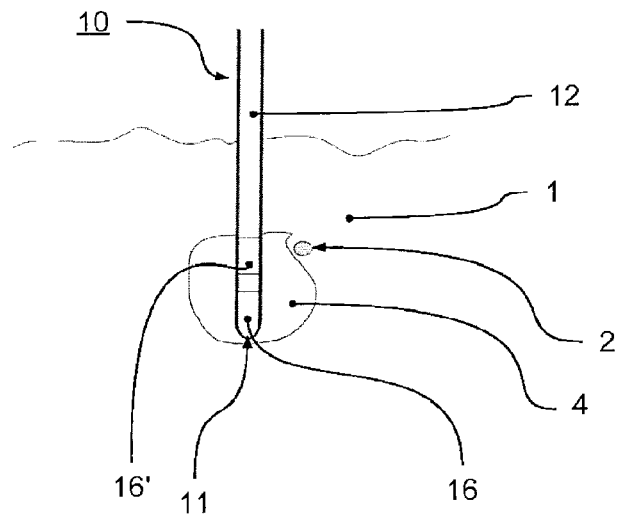
FIG. 2 illustrates a bipolar ablation probe in accordance with a disclosed embodiment, having a heat distribution field with stronger cooling in the proximal region.

FIG. 2 shows a first example embodiment of an ablation probe 10. The probe is a bipolar ablation probe 10 which has a first electrode 16 and a second electrode 16'. Both electrodes 16, 16' are located in a distal region of a probe body 12, close to a probe tip 11. The two electrodes 16, 16' are electrically insulated from one another.

As soon as a high-frequency current is applied to the electrodes 16, 16', a current distribution field is formed in the tissue 1 contacting the ablation probe 10. Provided the tissue 1 is homogeneous, this current distribution field is configured essentially spherically, wherein the current density decreases with increasing distance from the probe body 12. In the tissue, the high-frequency current performs work, which is manifested in the form of heat energy. Depending on the structure of the tissue 1, a heat distribution field is formed. Within the heat distribution field is a region in which the temperature increase is sufficiently high that the tissue becomes devitalized. This region is defined as the coagulation zone 4.

Irregular structures in the tissue 1, such as blood vessels, lymph ducts or organs can influence the current distribution field such that an asymmetrical heat distribution field is produced. An asymmetrical heat distribution field, and consequently an asymmetrical coagulation zone 4, is often undesirable.

In the example embodiment shown in FIG. 2, a blood vessel 2 is situated in the immediate vicinity of the ablation probe 10. With conventional ablation probes 10, this would result in a coagulation zone 4 having a high degree of asymmetry in the region of the blood vessel 2.

However, the ablation probe 10 according to the disclosed embodiments can counteract this effect. For this purpose, a second electrode 16', situated proximally behind the first electrode 16 is more strongly cooled. The approximately symmetrical coagulation zone 4 shown in FIG. 2 is thus formed.

Figure 3:
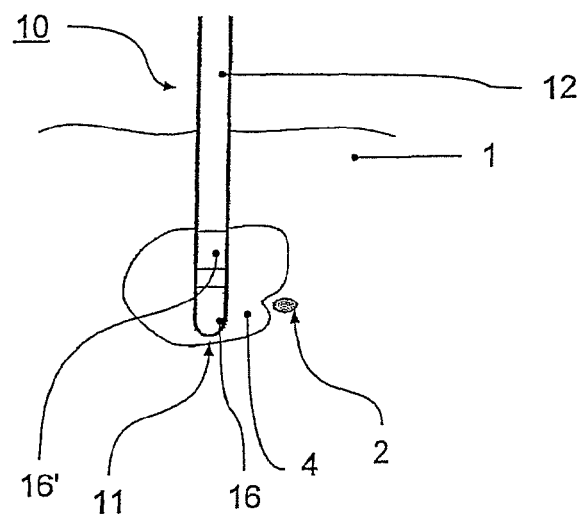
FIG. 3 illustrates a bipolar ablation probe in accordance with a disclosed embodiment, having a heat distribution field having stronger cooling in the distal region.

FIG. 3 shows a further example embodiment of the ablation probe 10. A blood vessel 2 is situated close to the first electrode 16 and thus in the immediate vicinity of the probe tip 11. Asymmetry of the coagulation zone 4 resulting therefrom can be counteracted by stronger cooling of the distal region of the ablation probe 10, that is, of the first electrode 16. Therefore, considering the heat distribution on the probe body 12, a maximum cooling performance (minimum temperature), which decreases in the proximal direction, is produced in the region of the probe tip 11. Distal introduction of the fluid into the evaporation region therefore results in a decreasing main pressure gradient in the proximal direction in the evaporation region.

Figure 4:
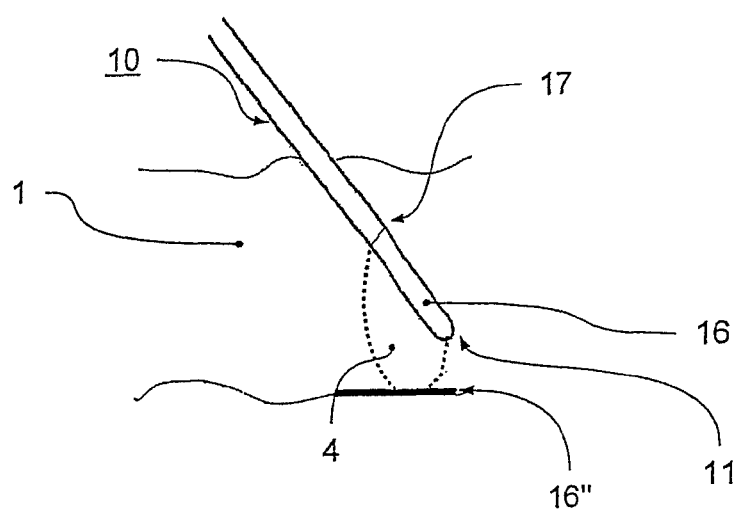
FIG. 4 illustrates a monopolar ablation probe in accordance with a disclosed embodiment, having a heat distribution field having stronger cooling in the distal region.

FIG. 4 shows a further example embodiment of the ablation probe 10. This is a monopolar probe 10. The ablation probe 10 includes therefore only one electrode 16. The second electrode for application of the high-frequency current is a neutral electrode 16", which is applied over a large area on a surface of the tissue 1. Depending on the position and orientation of the ablation probe 10 relative to the large area neutral electrode 16", a current distribution field is produced which depends on the distance between the electrodes 16, 16". In the example embodiment of FIG. 4, the current density in the tissue 1 close to the probe tip 11 is substantially higher than in regions which lie between a proximal end of the electrode 16 and the neutral electrode 16". Undesirable carbonization of the tissue 1 can therefore occur close to the probe tip 11. In order to prevent this effect, the ablation probe 10 according to the disclosed embodiment cools the probe body 12 more strongly in the region close to the probe tip 11. In particular, the distal region of the electrode 16 is more strongly cooled than a proximal region.

Positioning and orientation of the monopolar ablation probe 10 in which the proximal region of the electrode 16 must be more strongly cooled in order to create the most evenly decreasing heat distribution field possible are conceivable.

It is important for the disclosed embodiments to be able to adjust the heat distribution at the probe body 12 of the ablation probe 10. In particular, the ablation probe 10 can allow a maximum cooling effect to wander along the longitudinal axis thereof. It is therefore possible to set a maximum cooling zone at the tip 11 of the ablation probe 10. Alternatively, the cooling zone can be positioned close to the proximal end 17 of the electrode 16.

Figure 5:
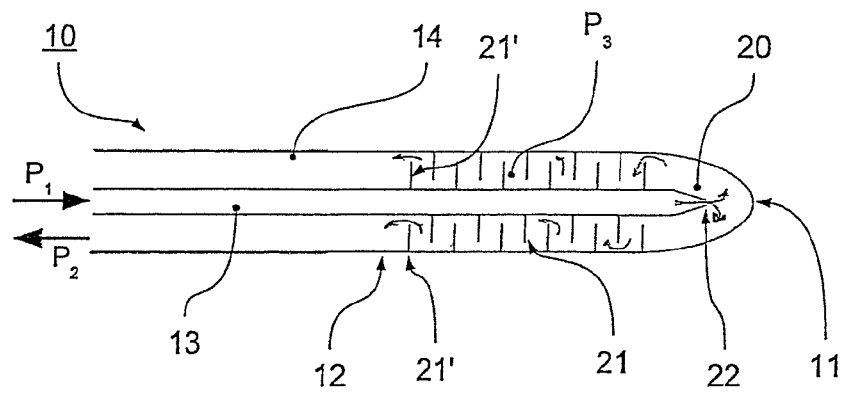
FIG. 5 illustrates a cross-section through an ablation probe in accordance with a disclosed embodiment, having resistance elements in a lamellar arrangement.
Figure 6:
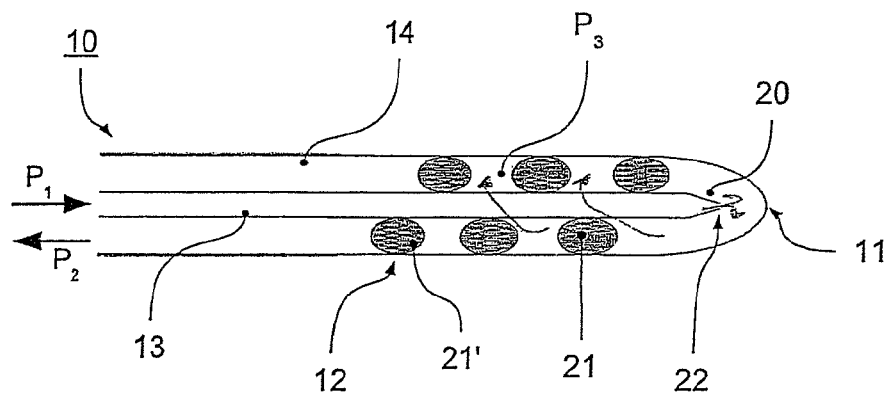
FIG. 6 is a cross-sectional view through an ablation probe in accordance with a disclosed embodiment, having spiral resistance elements.
Figure 7:
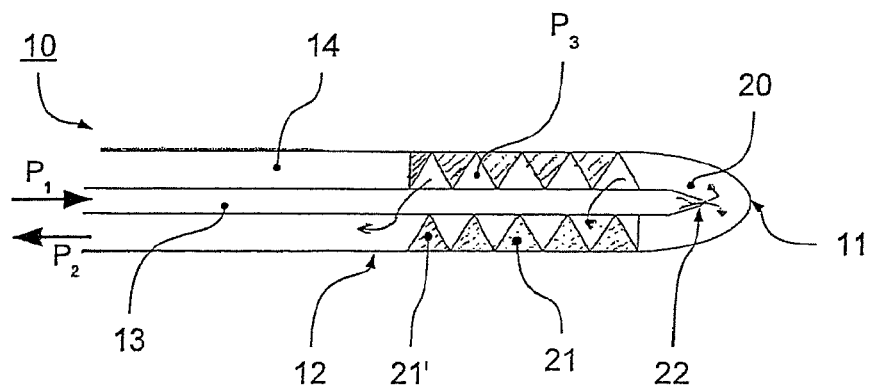
FIG. 7 is a cross-sectional view through an ablation probe in accordance with a disclosed embodiment, having triangular resistance elements.

The example embodiments of an ablation probe 10 shown in FIGS. 5 to 7 enable adjustment or positioning of the cooling center by means of the inlet pressure P1. These ablation probes 10 include an evaporation region 20 in which a refrigerant evaporates and the ablation probe 10, particularly the probe body 12, extracts heat energy. The evaporation region 20 extends from the probe tip 11 in the proximal direction along the longitudinal axis of the ablation probe 10.

The coolant is introduced into the evaporation region 20 via an inlet 13 close to the probe tip 11. Since the boiling point depends, according to the refrigerant, on the prevailing pressure and the temperature, the refrigerant evaporates at the given temperature only when a pressure P3 which is below the boiling pressure prevails in the evaporation region 20 close to the probe tip 11.

The evaporation region 20 includes a plurality of swirl elements 21, 21' which, according to FIG. 4, are arranged alternating in such a manner that, on the return route to the outlet 14, the coolant has to pass individual lamellae which form the swirl elements 21, 21'. As a result, turbulence is created. This turbulence improves, inter alia, the heat transfer between the refrigerant and the ablation probe 10, while it also causes flow resistance which increases depending on the inlet pressure P1.

Thus, with a low inlet pressure P1 just below the boiling pressure, there is only a low flow resistance. The refrigerant evaporates in the distal region of the evaporation region 20 close to an expansion nozzle 22. The main pressure gradient therefore falls below the boiling pressure in the distal region of the evaporation region. With increasing inlet pressure P1, the flow resistance increases. This results in back-pressure, which increases in the distal direction of the evaporation region 20. The swirl elements 21, 21' are arranged and configured such that the pressure P3 decreases in the direction of flow. Adjustment of the inlet pressure P1 such that evaporation of the refrigerant only takes place after the last swirl element 21' is thus conceivable. The pressure P3 of the main pressure gradient therefore remains above the boiling pressure until said last swirl element 21. Through variation of the inlet pressure P1, the main pressure gradient of the pressure P3 in the evaporation region 20 can be adjusted such that the zone of evaporation, that is, of maximum cooling can be positioned as desired.

FIGS. 6 and 7 show further example embodiments of the swirl elements 21, 21'. In FIG. 6, the evaporation elements 21, 21' are configured as a helix which winds round the inlet 13.

In FIG. 7, the swirl elements 21, 21' are configured with a saw-tooth form, projecting into the evaporation region.

It should be noted at this point that all the aforementioned parts are claimed as essential to the invention both alone and in any combination, particularly the details shown in the drawings. Amendments thereof are the common practice of persons skilled in the art.

The invention claimed is:

1. An electrosurgical device, comprising:
    a probe body;
    at least one electrode for applying a high-frequency current to a tissue;
    a cooling device including an evaporation region, the evaporation region being supplied with a fluid via an inlet to cool at least part of the probe body;
    an outlet to remove the fluid from the evaporation region;
    at least one dividing element that divides the evaporation region into at least one distal region and at least one proximal region, wherein the evaporation region is designed such that the relationship of the pressure between the proximal region and the distal region varies with an increasing pressure at the inlet; and
    a control device which adjusts the high-frequency current and which adjusts the inlet pressure at the inlet and/or outlet pressure at the outlet such that on application of the high-frequency current a prescribed heat distribution field is produced in the tissue, wherein the control device operates such that the inlet pressure is increased for a stronger cooling at the proximal region.

2. The electrosurgical device according to claim 1, wherein the electrical device is a probe for devitalizing the tissue and the high-frequency current generates tissue heating or a heat distribution field for devitalizing the tissue.

3. The electrosurgical device according to claim according to claim 2, wherein the cooling device influences the heat distribution field.

4. The electrosurgical device according to claim 1, wherein the at least one dividing element is a resistance element.

5. The electrosurgical device according to claim 1, wherein the at least one dividing element is a swirl element.

6. The electrosurgical device according to claim 1, wherein the plurality of dividing elements are arranged and configured such that a main pressure gradient is formed in the evaporation region along a longitudinal axis of the probe.

7. The electrosurgical device according to claim 6, wherein the main pressure gradient depends on the inlet pressure and/or the outlet pressure.

8. The electrosurgical device according to claim 5, wherein at least one of the swirl elements comprises an expansion element.

9. The electrosurgical device according to claim 8, wherein the expansion element is an expansion nozzle.

10. The electrosurgical device according to claim 1, wherein the prescribed heat distribution field is an approximately spherical heat distribution field.

11. A method for generating a prescribed heat distribution over a probe body of an electrosurgical device, the method comprising:
    feeding in a fluid for cooling the probe body via an inlet;
    introducing the fluid into an evaporation region from which heat is extracted by the fluid, the evaporation region being divided into at least one distal region and at least one proximal region;
    removing the fluid via an outlet; and
    varying the relationship of the pressure between the proximal region and the distal region such that the prescribed heat distribution field is produced in the tissue,
    wherein the inlet pressure is increased for a stronger cooling at the proximal region.

12. A method for generating a heat distribution field within a tissue, the method comprising:
    heating the tissue by the application of a high-frequency current with an electrosurgical device; and
    cooling the tissue with a probe body of the electrosurgical device,
    wherein the cooling comprises generating a prescribed heat distribution over the probe body, the prescribed heat distribution being generated by:
        feeding in a fluid for cooling the probe body via an inlet;
        introducing the fluid into an evaporation region from which heat is extracted by the fluid, the evaporation region being divided into at least one distal region and at least one proximal region;
        varying the relationship of the pressure between the proximal region and the distal region such that on application of the high-frequency current the prescribed heat distribution field is produced in the tissue, wherein the inlet pressure is increased for a stronger cooling at the proximal region; and
        removing the fluid via an outlet.

* * * * *

UNITED STATES PATENT AND TRADEMARK OFFICE
CERTIFICATE OF CORRECTION

PATENT NO. : 9,078,663 B2  Page 1 of 1
APPLICATION NO. : 13/003511
DATED : July 14, 2015
INVENTOR(S) : Geiselhart et al.

It is certified that error appears in the above-identified patent and that said Letters Patent is hereby corrected as shown below:

On the title page item [73], delete "ERBE ELEKTROMEDIZIN GMBH, Tucbingen (DE)" and insert -- ERBE ELEKTROMEDIZIN GMBH, Tuebingen (DE) --.

Signed and Sealed this
Twenty-second Day of December, 2015

Michelle K. Lee
*Director of the United States Patent and Trademark Office*